(12) United States Patent
Knodel

(10) Patent No.: US 8,070,034 B1
(45) Date of Patent: Dec. 6, 2011

(54) SURGICAL STAPLER WITH ANGLED STAPLE BAYS

(75) Inventor: Bryan D. Knodel, Flagstaff, AZ (US)

(73) Assignee: Cardica, Inc., Redwood City, CA (US)

( * ) Notice: Subject to any disclaimer, the term of this patent is extended or adjusted under 35 U.S.C. 154(b) by 0 days.

(21) Appl. No.: 12/781,746

(22) Filed: May 17, 2010

Related U.S. Application Data

(60) Provisional application No. 61/182,528, filed on May 29, 2009.

(51) Int. Cl.
*A61B 17/068* (2006.01)

(52) U.S. Cl. ............... 227/176.1; 227/175.1; 227/180.1; 227/19

(58) Field of Classification Search .... 227/175.1–182.1, 227/132–134, 19; 606/219
See application file for complete search history.

(56) References Cited

U.S. PATENT DOCUMENTS

| | | | | |
|---|---|---|---|---|
| 3,822,818 A | * | 7/1974 | Strekopytov et al. | 227/124 |
| 4,617,928 A | * | 10/1986 | Alfranca | 227/180.1 |
| 5,582,611 A | * | 12/1996 | Tsuruta et al. | 606/46 |
| 5,653,373 A | * | 8/1997 | Green et al. | 227/175.1 |
| 5,833,695 A | * | 11/1998 | Yoon | 606/139 |
| 7,070,083 B2 | * | 7/2006 | Jankowski | 227/176.1 |
| 7,217,285 B2 | * | 5/2007 | Vargas et al. | 623/1.36 |
| 7,422,138 B2 | * | 9/2008 | Bilotti et al. | 227/179.1 |
| 7,828,188 B2 | * | 11/2010 | Jankowski | 227/176.1 |
| 2003/0178465 A1 | * | 9/2003 | Bilotti et al. | 227/180.1 |
| 2007/0114261 A1 | * | 5/2007 | Ortiz et al. | 227/175.1 |
| 2008/0087707 A1 | * | 4/2008 | Jankowski | 227/176.1 |
| 2008/0190990 A1 | * | 8/2008 | Holsten et al. | 227/176.1 |
| 2010/0089973 A1 | * | 4/2010 | Kostrzewski | 227/180.1 |
| 2010/0213240 A1 | * | 8/2010 | Kostrzewski | 227/180.1 |

OTHER PUBLICATIONS

"Cardica Microcutter Implant Delivery Device 510(k), Cover Sheet, Table 10.1, "Substantial Equivalence Comparison," and Section 12, "Substantial Equivalence Discussion"", Oct. 18, 2010.

* cited by examiner

*Primary Examiner* — Lindsay Low
(74) *Attorney, Agent, or Firm* — Brian Schar

(57) ABSTRACT

An exemplary surgical stapler may include a staple holder including an upper surface, where the upper surface includes two substantially-planar angled surfaces positioned lateral to and angled relative to each other; staple bays within the staple holder, each opening to a corresponding angled surface; and staples, where at least one staple is held within at least one staple bay. Another exemplary surgical stapler may include a staple holder; a first group of staple bays defined within the staple holder, the first group of staple bays lying substantially in a first plane; and a second group of staple bays defined within the staple holder, the second plurality of staple bays lying substantially in a second plane; where the first plane intersects the second plane.

12 Claims, 2 Drawing Sheets

SURGICAL STAPLER WITH ANGLED STAPLE BAYS

This application claims priority to U.S. Provisional Patent Application Ser. No. 61/182,528, filed on May 29, 2009, which is herein incorporated by reference in its entirety.

FIELD OF THE INVENTION

The invention generally relates to surgical staplers and stapling.

BACKGROUND

Surgical staplers for use in minimally invasive surgery may be designed to be generally cylindrical in shape in order to fit through a corresponding trocar port placed in a patient, where that trocar port has a generally circular orifice defined therethrough. Such a surgical stapler typically includes a staple holder and an anvil pivotally connected to the staple holder. Referring to FIG. 1, a staple holder 2 viewed in cross-section may be generally shaped as a segment of a circle defined by a chord, which is the upper surface 4 of the staple holder 2 through which staples are ejected. Staples are held in individual bays or channels 6 within the staple holder 2. The bays or channels 6 are oriented perpendicular to the upper surface 4 of the staple holder 2. Consequently, the bays or channels 6 are oriented parallel to one another. Similarly, a knife slot 8 is typically defined in the staple holder 2, where that knife slot 8 is also oriented perpendicular to the upper surface 4 of the staple holder 2. The perpendicularity of the bays or channels 6 to the upper surface 4 limits the size of staples that can be deployed from the staple holder 2, because as the bays or channels 6 increase in size, they must move inward laterally such that they can still fit inside the staple holder 2. Further, by moving the bays or channels 6 laterally inward, space within the staple holder 2 laterally outward from those bays or channels 6 is wasted.

BRIEF DESCRIPTION OF THE DRAWINGS

The use of the same reference symbols in different figures indicates similar or identical items.

DETAILED DESCRIPTION

Figure 1:
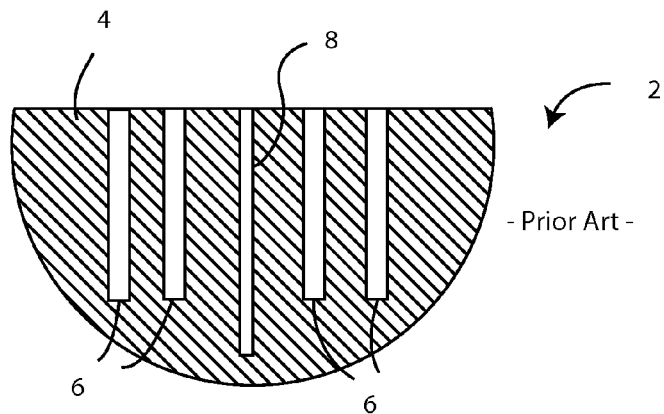
FIG. 1 is a cross-section end view of a prior art staple holder.
Figure 2:
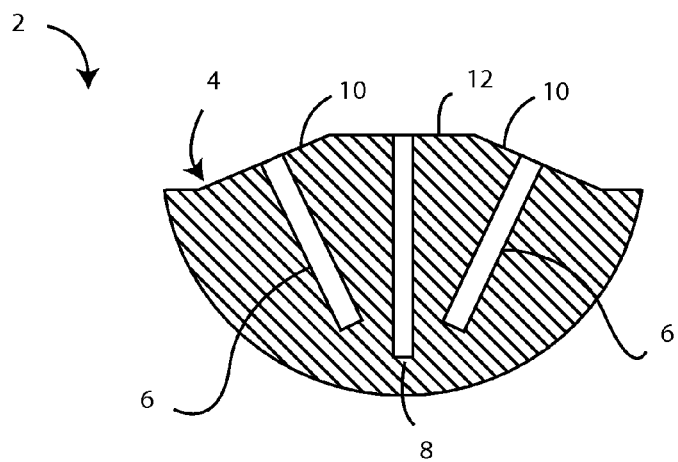
FIG. 2 is a cross-section end view of an exemplary staple holder with angled staple bays.

Referring to FIG. 2, a staple holder 2 may have an upper surface 4 that includes two angled surfaces 10. Each angled surface 10 is positioned lateral to the other. Each angled surface 10 may lie substantially in a different plane than the other, such that the two planes intersect. The upper surface 4 also may include a plateau surface 12 that connects the two angled surfaces 10. The angled surfaces 10 each may form an angle with the plateau surface 12. Alternately, the plateau surface 12 may be omitted, and the two angled surfaces 10 may directly intersect one another. At least one staple bay or channel 6 may be positioned relative to a corresponding angled surface 10 such that the upper end of that bay or channel 6 opens to that angled surface 10. Such a staple bay or channel 6 may be oriented substantially perpendicular to the angled surface 10, or may be oriented differently relative to the corresponding angled surface 10. Optionally, at least one staple bay or channel 6 may be oriented differently than at least one other staple bay or channel 6; the staple bays or channels 6 need not all have the same orientation relative to the angled surfaces 10 or each other. This angled orientation allows deeper staple bays or channels 6 to be defined in the staple holder 2 than in a staple holder 2 of the prior art of the same diameter. Further, the use of angled surfaces 10 increases the surface area of the upper surface 4 of the staple holder 2 as compared to the planar upper surface 4 of the prior art staple holder 2. In addition, by providing one or more bays or channels 6 in an angled configuration, those bays or channels 6 may be placed within the staple holder 2 in such a way that they can eject staples at a lateral distance further from the longitudinal center line of the staple holder 2 than the staple holders 2 of the prior art. Alternately, the staple holder 2 may have a substantially planar upper surface 4 such as shown in FIG. 1, and one or more staple bays or channels 6 may be oriented at an angle relative to that upper surface 4. At least one of the staple bays or channels 6 may form substantially a V-shape with regard to at least one other staple bay or channel 6 as viewed from the end. Optionally, a knife slot 8 may be defined in the staple holder 2, and may be located between staple bays or channels 6 as seen from the end.

Figure 3:
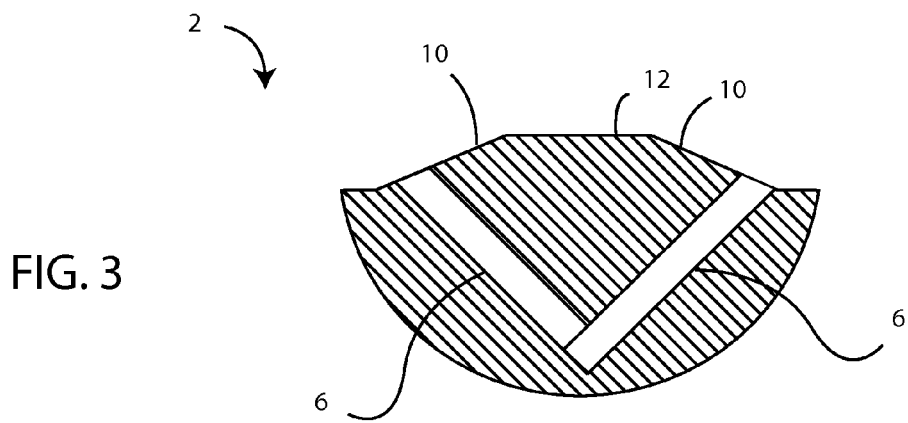
FIG. 3 is a cross-section end view of another exemplary staple holder with angled staple bays.

Referring also to FIG. 3, where staple bays 6 are used, the staple bays 6 may overlap one another as viewed from the end. Longitudinally, those staple bays 6 may be staggered to prevent interference between them. By overlapping two or more staple bays 6, even more efficiency may be obtained in the internal layout of the staple holder 2. In such a configuration, the knife slot 8 may be omitted, or if utilized, may be positioned above the staple bays 6 to prevent interference.

Figure 4:
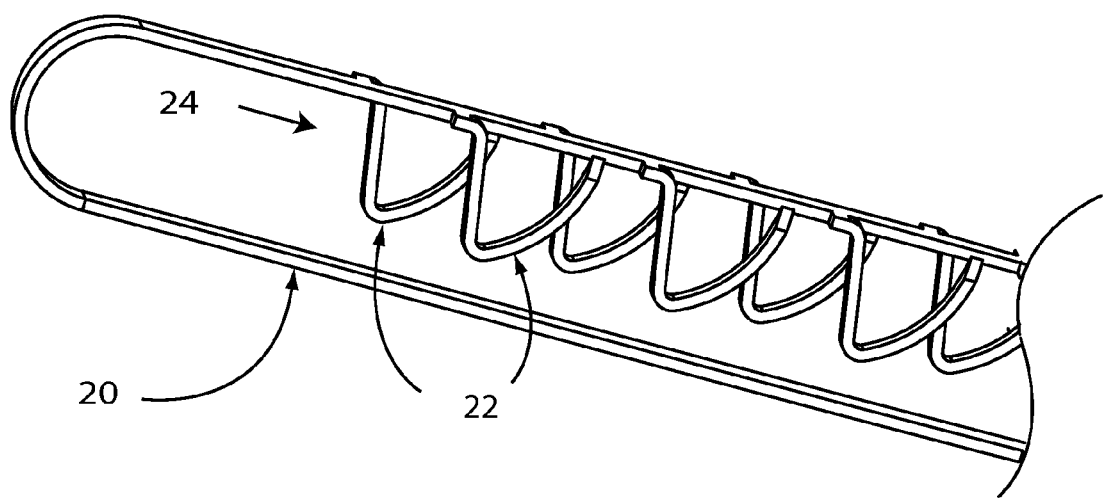
FIG. 4 is a perspective view of an exemplary feeder belt with staples frangibly affixed thereto.

Referring also to FIG. 4, any suitable staples, clips, or fasteners 22 may be ejected from the bays or channels 6. As one example, standard U-shaped or B-shaped staples or clips may be used. As another example, at least one feeder belt 20 with staples 22 fixed to and frangibly separated therefrom may be utilized; such a feeder belt may be as described in U.S. Patent Application Publication No. 2009/0065552, published on Mar. 12, 2009, which is hereby incorporated by reference herein in its entirety. One or more rows 24 of staples 22 may be connected to the feeder belt 20, and each row 24 of staples 22 may be oriented generally longitudinally.

While the invention has been described in detail, it will be apparent to one skilled in the art that various changes and modifications can be made and equivalents employed, without departing from the present invention. It is to be understood that the invention is not limited to the details of construction, the arrangements of components, and/or the steps of performing anastomosis set forth in the above description or illustrated in the drawings. Therefore, the invention is not to be restricted or limited except in accordance with the following claims and their legal equivalents.

What is claimed is:

1. A surgical stapler, comprising:
   a staple holder including an upper surface, said upper surface comprising two substantially-planar angled surfaces positioned lateral to and angled relative to each other;
   a plurality of staple bays within said staple holder, each opening to a corresponding said angled surface, wherein at least two said staple bays overlap one another as viewed along the longitudinal axis of said staple holder; and a plurality of staples, wherein at least one staple is held within at least one said staple bay.

2. The surgical stapler of claim 1, further comprising a carrier, wherein a plurality of staples are frangibly affixed to said carrier.

3. The surgical stapler of claim 1, wherein said angled surfaces lie in two different intersecting planes.

4. The surgical stapler of claim 3, wherein said planes intersect above the longitudinal centerline of said staple holder.

5. The surgical stapler of claim 3, wherein said planes intersect above the upper surface of said staple holder.

6. The surgical stapler of claim 1, wherein said angled surfaces face away from one another.

7. The surgical stapler of claim 1, wherein said angled surfaces form an obtuse angle relative to one another, as measured about the longitudinal axis of said staple holder and through said staple holder.

8. The surgical stapler of claim 1, further comprising a plateau surface between said angled surfaces, which connects said angled surfaces.

9. The surgical stapler of claim 1, wherein at least one said staple bay is oriented substantially perpendicular to the corresponding said angled surface.

10. The surgical stapler of claim 1, further comprising a longitudinally-extending knife slot defined in said staple holder, said knife slot located laterally between at least two said staple bays.

11. The surgical stapler of claim 1, wherein at least one said staple bay is oriented in a different direction than at least one other said staple bay.

12. The surgical stapler of claim 1, wherein said staple bays substantially form a V-shape as viewed along the longitudinal axis of said staple holder.

* * * * *